(12) United States Patent
Cohen et al.

(10) Patent No.: US 12,350,003 B2
(45) Date of Patent: Jul. 8, 2025

(54) SURGICAL DRAPE

(71) Applicant: MOMENTIS SURGICAL LTD., Or-Yehuda (IL)

(72) Inventors: Dvir Cohen, Ramot-Menashe (IL); Yaron Levinson, Tel-Aviv (IL)

(73) Assignee: Momentis Surgical Ltd, Or-Yehuda (IL)

( * ) Notice: Subject to any disclaimer, the term of this patent is extended or adjusted under 35 U.S.C. 154(b) by 41 days.

(21) Appl. No.: 16/132,544

(22) Filed: Sep. 17, 2018

(65) Prior Publication Data

US 2019/0083193 A1 Mar. 21, 2019

Related U.S. Application Data

(60) Provisional application No. 62/560,268, filed on Sep. 19, 2017.

(51) Int. Cl.
*A61B 46/10* (2016.01)
*A61B 46/00* (2016.01)
*A61B 46/20* (2016.01)
*A61B 46/23* (2016.01)

(52) U.S. Cl.
CPC .............. *A61B 46/10* (2016.02); *A61B 46/00* (2016.02); *A61B 46/23* (2016.02); *A61B 46/40* (2016.02); *A61B 2046/205* (2016.02)

(58) Field of Classification Search
CPC ......... A61B 46/00; A61B 46/10; A61B 46/20; A61B 46/23; A61B 46/27; A61B 46/30; A61B 46/40; A61B 2046/205; A61B 2046/234; A61B 1/00142; A61B 2017/00336; A61F 2013/15073

USPC .............. 128/849, 850, 852, 854, 855, 856; 604/356, 327; 600/121, 124, 123, 203
See application file for complete search history.

(56) References Cited

U.S. PATENT DOCUMENTS

| | | | |
|---|---|---|---|
| 5,178,162 A | * | 1/1993 | Bose ...................... A61B 46/27 |
| | | | 128/853 |
| 5,979,450 A | | 11/1999 | Baker et al. |
| 6,132,368 A | | 10/2000 | Cooper |
| 6,346,072 B1 | | 2/2002 | Cooper |
| 7,357,774 B2 | | 4/2008 | Cooper |

(Continued)

FOREIGN PATENT DOCUMENTS

| | | |
|---|---|---|
| CN | 105852976 | 8/2016 |
| DE | 102015224986 A1 * | 4/2017 |

(Continued)

OTHER PUBLICATIONS

Machine translation of DE102015224986A1 (Year: 2017).*

(Continued)

*Primary Examiner* — Caitlin A Carreiro
(74) *Attorney, Agent, or Firm* — Momentum IP; Marc Van Dyke

(57) ABSTRACT

A folded surgical drape, including:
a tubular axially collected sheath having a distal end and a proximal end and a lumen between said distal end and said proximal end, wherein the axially collected sheath comprising at least one distal opening axially collected into said lumen and, wherein the axially collected sheath is axially folded to form at least one valley fold surrounding the distal opening sized and shaped for insertion of the user's hands on both sides of the distal opening.

29 Claims, 9 Drawing Sheets

(56) References Cited

U.S. PATENT DOCUMENTS

| | | | |
|---|---|---|---|
| 7,666,191 B2 | 2/2010 | Orban, III et al. | |
| 7,699,855 B2 | 4/2010 | Anderson et al. | |
| 7,727,244 B2 | 6/2010 | Orban, III et al. | |
| 7,819,885 B2 | 10/2010 | Cooper | |
| 7,886,743 B2 | 2/2011 | Cooper et al. | |
| 7,963,913 B2 | 6/2011 | Devengenzo et al. | |
| 8,105,338 B2 | 1/2012 | Anderson et al. | |
| 8,182,469 B2 | 1/2012 | Anderson et al. | |
| 8,202,278 B2 | 6/2012 | Orban, III et al. | |
| 8,206,406 B2 | 6/2012 | Orban, III | |
| 8,216,250 B2 | 7/2012 | Orban, III et al. | |
| 8,220,468 B2 | 7/2012 | Cooper et al. | |
| 8,273,076 B2 | 9/2012 | Devengenzo et al. | |
| 8,529,582 B2 | 9/2013 | Devengenzo et al. | |
| 8,672,922 B2 | 3/2014 | Loh et al. | |
| 8,746,252 B2 | 6/2014 | McGrogan et al. | |
| 2002/0151848 A1* | 10/2002 | Capote, Jr. | A61B 46/10 604/263 |
| 2006/0161137 A1* | 7/2006 | Orban, III | A61B 46/10 606/1 |
| 2008/0119803 A1* | 5/2008 | Lund | A61M 27/008 604/327 |
| 2010/0275929 A1 | 11/2010 | Kaska | |
| 2010/0317936 A1* | 12/2010 | Al-Ali | A61B 46/10 600/323 |
| 2011/0041995 A1* | 2/2011 | Adams | A61B 46/13 156/60 |
| 2011/0146694 A1* | 6/2011 | Fischer | A61B 46/27 128/856 |
| 2011/0168189 A1 | 7/2011 | Cooper | |
| 2012/0097176 A1 | 4/2012 | Pitaoulis | |
| 2013/0167847 A1* | 7/2013 | Rogers | A61F 5/37 294/81.1 |
| 2015/0202009 A1 | 7/2015 | Nussbaumer | |
| 2015/0257841 A1 | 9/2015 | Dachs, II | |
| 2018/0214228 A1 | 8/2018 | Toure et al. | |
| 2022/0087764 A1 | 3/2022 | Levinson et al. | |

FOREIGN PATENT DOCUMENTS

| | | |
|---|---|---|
| JP | 2006-43128 | 2/2006 |
| JP | 2009-509653 | 3/2009 |
| JP | 2009-153859 | 7/2009 |
| JP | 2015-93142 | 5/2015 |
| JP | 2016-64449 | 4/2016 |
| JP | 2016-179103 | 10/2016 |
| JP | 2018-166639 | 11/2018 |
| WO | WO 2011/154010 | 12/2011 |
| WO | WO 2018/208898 | 11/2018 |
| WO | WO 2020/141517 | 7/2020 |

OTHER PUBLICATIONS

International Search Report and the Written Opinion Dated Mar. 23, 2020 From the International Searching Authority Re. Application No. PCT/IL2019/051437. (40 Pages).

International Preliminary Report on Patentability Dated Jul. 15, 2021 From the International Bureau of WIPO Re. Application No. PCT/IL2019/051437. (10 Pages).

Supplementary European Search Report and the European Search Opinion Dated Aug. 31, 2022 From the European Patent Office Re. Application No. 19906895.8. (8 Pages).

Examination Report Under Sections 12 & 13 of the Patents Act, 1970 and the Patents Rules, 2003 Dated Mar. 22, 2023 From the Government of India, Intellectual Property India, Patents, Designs, Trade Marks, Geographical Indications, The Patent Office Re. Application No. 202127031455. (9 pages).

Translation Dated Nov. 24, 2023 of Notification of Office Action Dated Oct. 23, 2023 From the National Intellectual Property Administration of the People's Republic of China Re. Application No. 201980092375.6 (13 Pages).

Notification of Office Action and Search Report Dated Oct. 23, 2023 From the National Intellectual Property Administration of the People's Republic of China Re. Application No. 201980092375.6 and Its Machine Translation Into English. (24 Pages).

Notice of Reason(s) for Rejection Dated Oct. 17, 2023 From the Japan Patent Office Re. Application No. 2021-538022 and Its Translation Into English. (7 Pages).

* cited by examiner

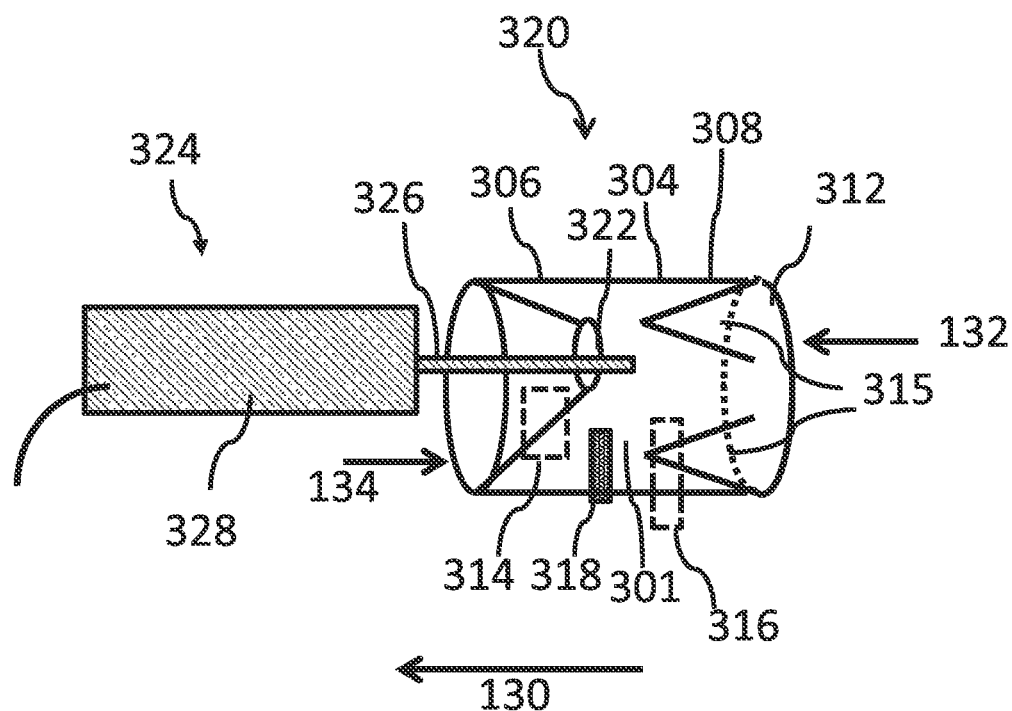
FIG. 3A
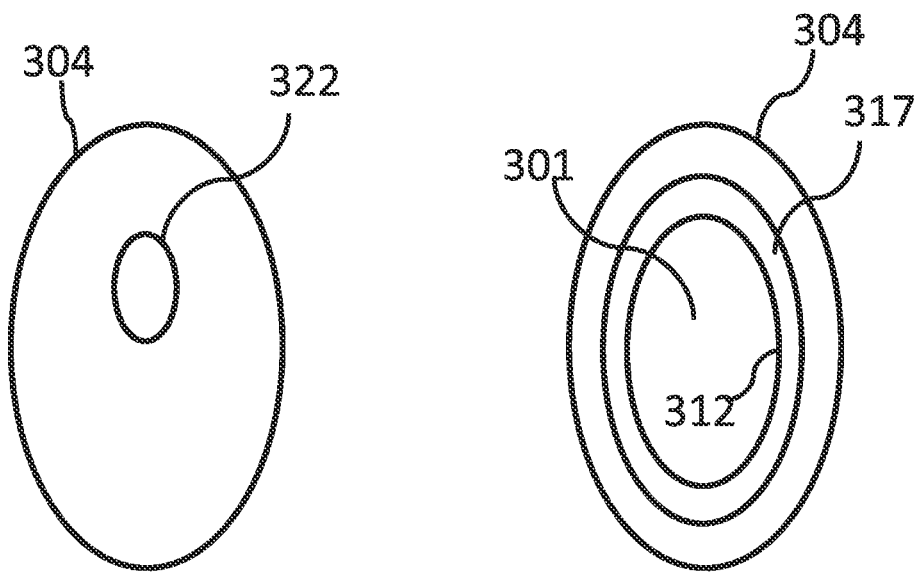
FIG. 3B
FIG. 3C

SURGICAL DRAPE

RELATED APPLICATION

This application claims the benefit of priority under 35 USC § 119(e) of U.S. Provisional Patent Application No. 62/560,268 filed on Sep. 19, 2017, the contents of which are incorporated by reference as if fully set forth herein in their entirety.

FIELD AND BACKGROUND OF THE INVENTION

The present invention, in some embodiments thereof, relates to a drape and, more particularly, but not exclusively, to a surgical drape for covering surgical devices.

SUMMARY OF THE INVENTION

Some examples of some embodiments of the invention are listed below:

Example 1. A folded surgical drape, comprising:
  a tubular axially collected sheath having a distal end and a proximal end and a lumen between said distal end and said proximal end, wherein said axially collected sheath comprising at least one distal opening axially collected into said lumen and, wherein said axially collected sheath is axially folded to form at least one valley fold surrounding said distal opening sized and shaped for insertion of the user's hands on both sides of said distal opening.

Example 2. The folded surgical drape of example 1, wherein said tubular axially collected sheath is at least partially transparent.

Example 3. The folded surgical drape of example 2, comprising at least one visible marking on said axially collected sheath near said distal opening or surrounding said distal opening, wherein said marking is positioned inside said lumen and is visible through said at least partially transparent sheath.

Example 4. The folded surgical drape of any one of examples 1 to 3, comprising at least one visible marking on said axially collected sheath designed for indicating the position of said at least one valley fold or said proximal end.

Example 5. The folded surgical drape of any one of examples 1 to 4, wherein a length of said axially collected surgical drape is at least 50% smaller than the length of said axially collected surgical drape in an axially extended state.

Example 6. The folded surgical drape of any one of examples 1 to 5, wherein a volume of said axially collected surgical drape is at least 90% smaller than the volume of said axially collected surgical drape in an axially extended state.

Example 7. A method for covering a surgical device having an extension, comprising:
  inserting an extension of said surgical device through a distal opening of an axially collected tubular sheath into a lumen of said axially collected tubular sheath;
  axially extending said tubular sheath while covering at least a portion of said surgical device;
  closing said distal opening by at least one distal fastener attached to said tubular sheath near or around said distal opening.

Example 8. The method of example 7, comprising:
  aligning said distal opening with said extension of said surgical device by introducing at least part of a user hand into a valley fold in said axially collected tubular sheath prior to said inserting.

Example 9. The method of examples 7 or 8, wherein said closing comprises fastening a portion of said tubular sheath by at least one proximal fastener.

Example 10. The method of any one of examples 7 to 9, wherein said axially extending comprises inverting the tubular sheath during said covering of said at least a portion of said surgical device.

Example 11. The method of any one of examples 7 to 10, wherein said axially extending comprises axially extending said tubular sheath while covering at least part of a stabilizing arm connected to said surgical device.

Example 12. The method of any one of examples 7 to 11, wherein said inserting comprises, inserting said extension through said distal opening into said lumen of said axially collected tubular sheath and out of said lumen through a proximal opening of said axially collected tubular sheath.

Example 13. A surgical drape for covering a surgical device having an extension, comprising:
  a thin tubular flexible sheath having a distal opening and a proximal opening, wherein said distal opening has a smaller aperture compared to an aperture of said proximal opening, and wherein said distal opening aperture is larger than a width of an extension of a surgical device;
  at least one distal fastener positioned near said distal opening, and configured to close said distal opening aperture.

Example 14. The surgical drape of example 13, comprising at least one handling portion configured to allow manipulation of said thin tubular flexible sheath by hand.

Example 15. The surgical drape of example 14, wherein said at least one handling portion comprises at least one axial valley fold sized and shaped for insertion of at least part of a hand.

Example 16. The surgical drape of examples 14 or 15, wherein said at least one handling portion comprises at least one slot formed in a surface of said thin tubular flexible sheath.

Example 17. The surgical drape of any one of examples 14 to 16, wherein said at least one handling portion comprises a strap and/or a handle connected to said thin tubular flexible sheath.

Example 18. The surgical drape of example 17, wherein said at least one handling portion is a detachable handling portion.

Example 19. The surgical drape of any one of examples 13 to 18, wherein said thin tubular flexible sheath radially folds to form a plurality of concertina folds.

Example 20. The surgical drape of any one of examples 13 to 19, comprising at least one visible marking designed to mark said distal opening and/or a distal end of said thin tubular flexible sheath.

Example 21. The surgical drape of example 20, wherein said at least one visible marking comprises a sticker.

Example 22. The surgical drape of example 20, wherein said at least one visible marking is a color marking.

Example 23. The surgical drape of any one of examples 13 to 22, comprising at least one proximal fastener positioned at an axial distance of at least 10 cm from said proximal opening aperture.

Example 24. The surgical drape of any one of examples 13 to 23, wherein said at least one distal fastener comprises a strap or an adhesive tape attached to the outer surface of said thin tubular flexible sheath.

Example 25. The surgical drape of any one of examples 13 to 24, wherein said at least one distal fastener comprises a Velcro tape attached to the outer surface of said thin tubular flexible sheath.

Example 26. The surgical drape of example 23, wherein said at least one proximal fastener comprises a strap or an adhesive tape attached to the outer surface of said thin tubular flexible sheath.

Example 27. The surgical drape of example 23, wherein said at least one proximal fastener comprises a Velcro tape attached to the outer surface of said thin tubular flexible sheath.

Example 28. The surgical drape of any one of examples 13 to 27, wherein said thin tubular flexible sheath is made from at least a partly transparent material.

Example 29. The surgical drape of any one of examples 13 to 28, wherein said thin tubular flexible sheath comprises at least one transparent section sized for visualizing at least a portion of said surgical device.

Example 30. The surgical drape of any one of examples 13 to 29, wherein axially collecting said thin tubular flexible sheath reduces the axial length of said thin tubular flexible sheath by at least 50%.

Example 31. The surgical drape of any one of examples 13 to 30, wherein said thin tubular flexible sheath has a circular or elliptical cross-section.

Example 32. The surgical drape of any one of examples 13 to 31, wherein said thin tubular flexible sheath has a rectangular cross-section.

Example 33. The surgical drape of any one of examples 13 to 32, wherein said thin tubular flexible sheath is made from a continuous plastic sheath.

Example 34. The surgical drape of any one of examples 13 to 33, wherein said thin tubular flexible sheath is made from at least two welded plastic sheaths.

Example 35. The surgical drape of any one of examples 13 to 34, wherein said distal fastener has a length of at least 15 cm.

Example 36. The surgical drape of example 23, wherein said proximal fastener had a length of at least 15 cm.

Example 37. The surgical device of any one of examples 13 to 36, wherein said distal fastener is positioned in a distance of up to 10 cm from said distal opening.

Example 38. A surgical drape for covering a surgical device having an extension, comprising:
  a thin tubular flexible sheath having a distal opening and a proximal opening, wherein said distal opening has a smaller aperture compared to an aperture of said proximal opening, and wherein said distal opening aperture is larger than a width of an extension of a surgical device;
  a proximal fastener positioned at a distance of at least 20 cm from said distal opening and said proximal opening, shaped and sized to narrow a lumen of said surgical drape by at least 25% when fastened around said surgical drape.

Example 39. The surgical drape of example 38, wherein said proximal fastener is a movable proximal fastener configured to axially move on the surgical drape to a desired location.

Example 40. The surgical drape of examples 38 or 39, comprising a distal fastener configured to close said distal opening.

Example 41. A method for covering a surgical device, comprising:
  axially extending an axially collapsed tubular sheath having a proximal opening and a distal opening while covering at least a portion of said surgical device;
  closing said distal opening and said proximal opening while leaving at least part of said surgical device axially collapsed.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 3A is a schematic representation of an axially collected surgical drape, according to some embodiments of the invention;

FIG. 3B is a schematic distal view representation of an axially collected surgical drape, according to some embodiments of the invention;

FIG. 3C is a schematic proximal view representation of an axially collected surgical drape, according to some embodiments of the invention;

DESCRIPTION OF SPECIFIC EMBODIMENTS OF THE INVENTION

Figure 1A:
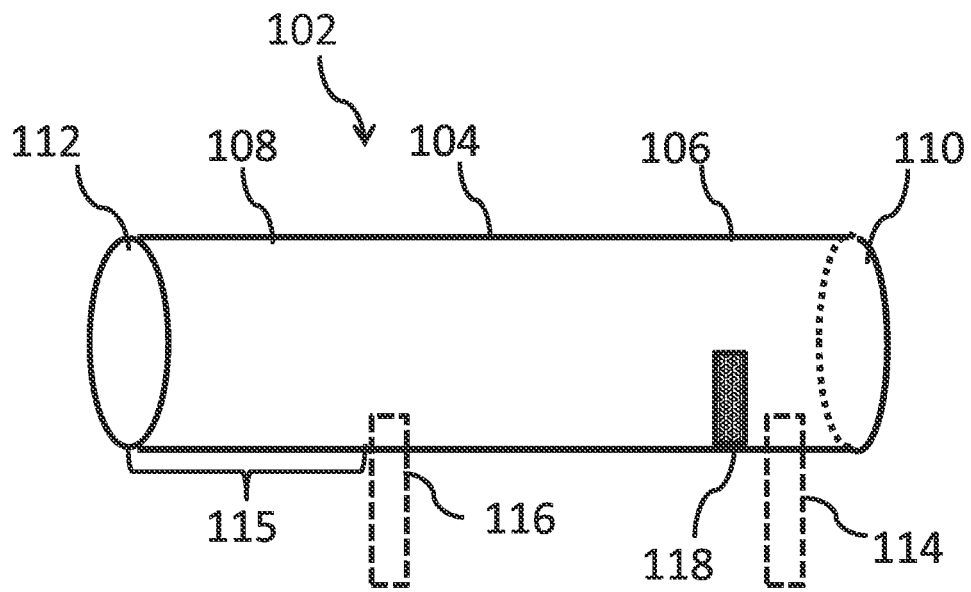
FIGS. 1A and 1B are schematic block diagrams of an axially extended surgical drape, according to some embodiments of the invention.

The present invention, in some embodiments thereof, relates to a drape and, more particularly, but not exclusively, to a surgical drape for covering surgical devices.

An aspect of some embodiments of the present invention relates to covering a surgical device by axially extending a surgical drape around the surgical device. In some embodiments, the surgical drape is axially collected, for example to decrease the length of the axially extended surgical drape by at least 50%, for example by at least 50%, by at least 60%, by at least 70%, by at least 80% or any intermediate or larger percentage. In some embodiments, the surgical drape is axially collected, for example to decrease the length of an axially extended drape from at least 2 meters to 1 meter or any intermediate or shorter length in an axially collected state. In some embodiments, the surgical drape is axially collected, for example to decrease the volume of the axially extended surgical drape by at least 90%, for example by at least 90%, by at least 92%, by at least 95% or any intermediate or larger percentage. In some embodiments, when the surgical drape is axially collected, at least one opening for insertion of the surgical device is axially collected into a lumen of the surgical drape. Optionally, axially collecting the at least one opening allows minimizing damage to the opening when the surgical drape is stored or not in use.

According to some embodiments, when the surgical drape is axially collected, at least one axial valley fold is formed, optionally spaced apart from the at least one opening. In some embodiments, the at least one valley fold is shaped and sized for placing at least part of a user's hand, for example the fingers of the user.

According to some embodiments, the at least one valley fold formed in the axially collected surgical drape directs a surgical drape coverage by marking a location for insertion of the user's hands. In some embodiments, the valley fold marks a proximal opening of the surgical drape. Optionally, the surgical drape comprises at least one visible marking, for example a color marking near or around the distal opening of the surgical drape. Possible advantages of having valley folds shaped and sized for insertion at least part of a user's hand at one end of the surgical drape, is that they allow a user of the surgical drape to hold the axially collected surgical drape in a correct orientation and/or to direct the coverage of a surgical device.

According to some embodiments, the surgical drape comprises a plurality of radial concertina folds, also termed zig-zag or z-shaped folds. In some embodiments, the surgical drape comprises at least one handling portion, for example a handle or a strap attached to the surgical drape and is sized and shaped for handling the surgical drape. Optionally, the handling portion is a detachable handling portion configured to detach from the surgical drape or from the tubular sheath of the surgical drape, for example when the covering process is over.

According to some embodiments, when the surgical drape is axially collected, a distal opening of the surgical drape is positioned near a proximal opening of the surgical drape, for example to minimize the axial length or the volume of the axially collected surgical drape. A distal opening is an opening which is adjacent to an extension of the surgical device, when the surgical drape is axially extended. A proximal opening is an opening distant from the extension of the surgical device, when the surgical drape is axially extended. In some embodiments, when the drape is axially collected, the distal opening of the drape is positioned at an axial distance of less than 15 cm from the proximal opening, for example less than 15 cm, less than 10 cm, less than 5 cm or any intermediate or smaller distance. In some embodiments, when axially extending the axially collected surgical drape, the distal opening moves to a distant position from said proximal opening, for example to a distance of at least 30 cm from said proximal opening, for example at least 30 cm, at least 40 cm, at least 50 cm, at least 60 cm or any intermediate or larger distance from the proximal opening. In some embodiments, when the axially collected surgical drape is axially extended, the surgical drape or the tubular sheath of the surgical drape is inverted. In some embodiments, when the surgical drape is axially extended and inverted, an outer surface of the axially collected surgical drape becomes an inner surface of the axially extended surgical drape.

An aspect of some embodiments of the present invention relates to covering a surgical device having an extension by inserting the surgical device extension through an opening in a tubular sheath, which is optionally a thin tubular flexible sheath and axially extending the tubular sheath while covering the surgical device. In some embodiments, the opening is closed, for example to prevent contamination of the surgical device with biological fluids or other biological materials during a surgery. In some embodiments, the tubular sheath is made from a continuous plastic sheath. Alternatively, the tubular sheath is made from at least two welded plastic sheaths.

According to some embodiments, the opening in the sheath which is shaped and sized for insertion of the surgical device extension, for example a distal opening is wider than the width of the extension, and optionally narrower than a width of the surgical device body. Alternatively, the distal opening of the surgical drape is wider from the width of the device extension and from the width of the device body.

According to some embodiments, to close the distal opening, which is positioned around the device extension, a distal fastener is fastened. In some embodiments, the distal fastener fastens the surgical drape and/or the distal opening of the surgical drape to the device extension. the In some embodiments, the distal fastener is positioned near the distal opening, for example at an axial distance of up to 15 cm, for example up to 15 cm, up to 10 cm, up to 5 cm or any intermediate or smaller value. Alternatively, the distal fastener is positioned around the distal opening.

According to some embodiments, to fasten the surgical drape around the device body, a proximal fastener is fastened. In some embodiments, the proximal fastener is positioned near the proximal opening, for example at an axial distance of up to 10 cm, for example up to 10 cm, up to 5 cm, up to 2 cm or any intermediate or shorter distance. Alternatively, the proximal fastener is axially spaced apart from the proximal opening of the surgical drape. In some embodiments, the proximal fastener is positioned at a distance of at least 10 cm from the proximal opening, for example at least 10 cm, at least 15 cm, at least 20 cm, at least 30 cm or any intermediate or longer distance. A possible advantage of having a proximal fastener positioned at a distance from the proximal opening of the surgical drape is that it leaves a proximal portion of the surgical drape loose and partly axially collected. In some embodiments, this loose proximal portion covers at least one fixation arm connected to the surgical device body. In some embodiments, when the surgical device moves in a linear direction, the loose proximal portion of the surgical drape straightens and axially extends without tearing the surgical drape.

According to some embodiments, the tubular sheath comprises a distal opening and a proximal opening at two ends of the tubular sheath. In some embodiments, the tubular sheath has a circular, elliptical or a rectangular cross-section. In some embodiments, the distal opening is shaped and sized to allow insertion of the surgical device extension and the proximal opening is shaped and sized to surround the device body. In some embodiments, the diameter and/or the aperture of the distal opening is larger than the diameter and/or the width of the device extension. Optionally, the diameter and/or the aperture of the distal opening are smaller than the width of the device body. In some embodiments, the proximal opening has a diameter and/or an aperture larger than the width of the device body, for example to allow enclosing of the entire device body by the drape.

According to some embodiments, the surgical drape is a foldable drape, for example an axially collectable surgical drape. In some embodiments, the surgical drape comprises at least one visible marking, optionally a colored marking for example to indicate the position of the distal opening and/or the distal end of the drape. In some embodiments, a visible marking of the distal opening allows for example to easily direct the device extension through the distal opening when the surgical drape is axially collected.

According to some embodiments, the surgical drape comprises at least one axial valley fold. Optionally, the surgical drape comprises at least two valley folds. In some embodiments, one of the at least two valley folds includes the distal opening of the surgical drape. In some embodiments, the second of the at least two axial valley folds is shaped and sized to allow insertion of at least part of a user's hand, for example the fingers of the users. In some embodiments, the user inserts at least part of his hand into the valley fold, for example to hold the surgical drape and/or to direct the covering process of the surgical device.

According to some embodiments, the surgical drape comprises at least one handling portion configured to allow manipulation of the tubular sheath by hand. In some embodiments, the at least one handling portion comprises a handle or a strap. Alternatively or additionally, the at least one handling portion comprises at least one slot formed in the surface of the tubular sheath or at least one fold, for example a valley fold. Optionally, the handling portion is a detachable handling portion designed to detach from the surgical drape once the covering process is over.

An aspect of some embodiments relates to fastening a surgical drape to a surgical device while leaving part of the surgical drape loose and/or axially collected. In some embodiments, a part of the surgical drape between a distal fastener and a proximal fastener remains loose and/or at least partly axially collected. Alternatively or additionally, a part of the surgical drape between a proximal fastener and a proximal opening of the surgical drape remains loose and/or axially collected. In some embodiments, a part of the surgical drape covering a movable element, for example an extending and/or a rotating element connected to the surgical device is unfastened. In some embodiments, the surgical drape is not fastened to the movable element, for example to prevent tearing of the surgical drape while the movable element moves.

According to some embodiments, a surgical drape having a distal opening and a proximal opening comprises at least one proximal fastener, positioned at a desired distance from the proximal opening. In some embodiments, the proximal fastener is positioned between the distal opening and the proximal opening of the surgical drape. In some embodiments, the proximal fastener is positioned at an axial distance of at least 20 cm from the proximal opening, for example at least 20 cm, at least 40 cm, at least 60 cm, at least 80 cm or any intermediate or longer distance.

In some embodiments, the surgical drape comprises at least one distal fastener, positioned near the distal opening of the surgical drape, for example at an axial distance of up to 20 cm from the distal opening. In some embodiments, the proximal fastener is positioned between the proximal opening and the distal fastener. In some embodiments, the proximal fastener is positioned at an axial distance of at least 30 cm from the distal fastener, and at an axial distance of at least 20 cm from the proximal opening.

According to some embodiments, the proximal fastener is a movable proximal fastener. In some embodiments, a user of the surgical drape can determine the length of the unfastened part of the surgical drape by positioning the movable proximal fastener at a desired location on the surgical drape.

According to some embodiments, the proximal fastener is shaped and sized to constrict a lumen of the surgical drape by at least 20%, for example by at least 20%, by at least 30%, by at least 40%, by at least 50%, by at least 60%, by at least 70% or any intermediate or larger percentage, when fastened around the surgical drape. In some embodiments, when the proximal fastener is fastened a portion of the surgical drape between the proximal fastener and the proximal opening of the surgical drape is unfastened, and optionally at least partly axially collected.

According to some embodiments, the surgical drape or the thin tubular flexible sheath which comprised in the surgical drape is elastic, for example to allow a better form fitting to the surgical fitting. Alternatively, the surgical drape or the thin tubular flexible sheath which comprised in the surgical drape is non-elastic, for example to allow easier covering of the surgical device.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Surgical Drape

According to some exemplary embodiments, a surgical drape is designed to cover and isolate portions of surgical devices unnecessary for a surgical procedure, while keeping other portions of the device that can be used during the procedure uncovered, for example to minimize contamination of the device with biological material, for example biological fluids. Additionally, the surgical drape is used to separate between sterile and non-sterile components, for example to maintain sterility during surgical procedures.

Figure 1B:
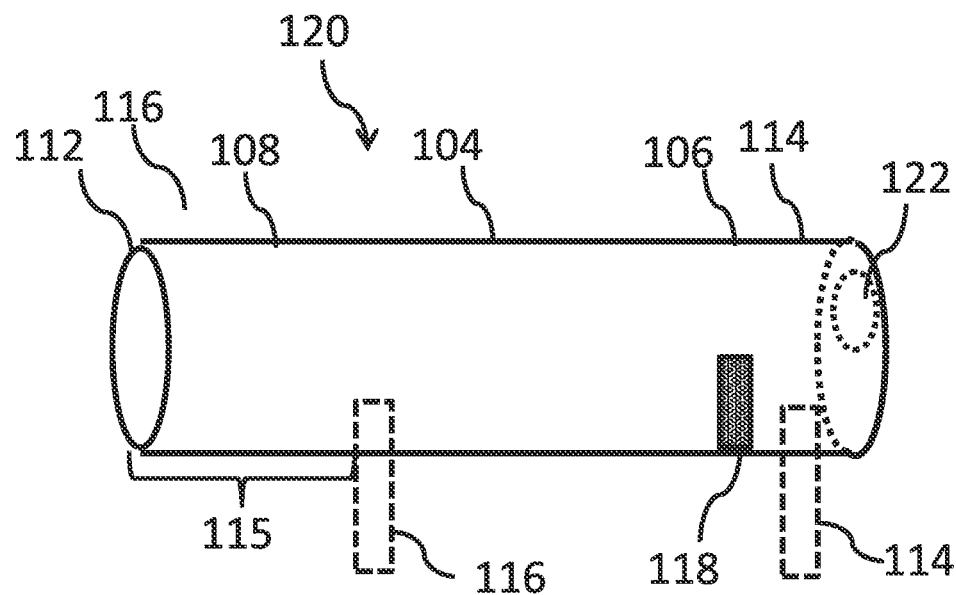

Reference is now made to FIGS. 1A and 1B, describing a surgical drape in an axially extended state, according to some exemplary embodiments of the invention. According to some exemplary embodiments, a surgical drape 102, comprises a surgical drape body 104 having a distal end 106 and a proximal end 108. In some embodiments, the surgical drape body 104 comprises a distal opening 110 at the distal end 106 of the surgical drape 102 and a proximal opening 112 at the proximal end 112 of the surgical drape 102.

According to some exemplary embodiments, the surgical drape body 104 is tubular with a circular cross-section or a rectangular cross-section. In some embodiments, the surgical drape is foldable and optionally is made from plastic or cloth optionally in a grade suitable for usage during surgical procedures. In some embodiments, the surgical drape is made from a transparent material. Alternatively, the surgical drape comprises at least one transparent section, for example to visualize at least one portion of the device.

According to some exemplary embodiments, the surgical drape 102 comprises at least one distal fastener 114 near or around the distal opening 110, configured to close the distal opening 110. In some embodiments, the distal fastener 114 is positioned at an axial distance of up to 15 cm from the distal opening 110, for example up to 15 cm, up to 10 cm, up to 5 cm or any intermediate or shorter distance. In some embodiments, the distal fastener length is at least 10 cm, for example at least 15 cm, at least 20 cm, at least 25 cm or any intermediate or larger value. In some embodiments, at least one distal fastener 114 is attached to the surface of the surgical drape or placed in a channel within the drape, optionally surrounding the distal opening. In some embodiments, the at least one distal fastener comprises an adhesive tape, a string or any elongated element that allows closure of the distal opening. Optionally, the at least one distal fastener prevents unintentional opening of the distal opening.

According to some exemplary embodiments, the surgical drape 102 comprises at least one proximal fastener 116 positioned at an axial distance 115 of at least 15 cm from the proximal opening 112, for example at least 15 cm, at least 20 cm, at least 25 cm or any intermediate or larger value. In some embodiments, the proximal fastener 116 is shaped and sized to fasten a portion of the surgical drape 102, optionally around part of a surgical device. Alternatively, the proximal fastener is positioned near or around the proximal opening, and is shaped to allow closure of the proximal opening. In some embodiments, the at least one proximal fastener 116 is attached to the surface of the surgical drape or placed in a channel within the surgical drape 102, optionally surrounding the surgical drape 102. In some embodiments, the at least one proximal fastener comprises an adhesive tape, a string or any elongated element that allows the wrapping of the fastener around the proximal opening and prevents unintentional opening of the proximal opening. In some embodiments, the length of the proximal fastener 116 is at least 10 cm, for example at least 10 cm, at least 15 cm, at least 20 cm, at least 25 cm or any intermediate or larger value.

According to some exemplary embodiments, the surgical drape 102 comprises at least one marking, optionally a visible marking, for example marking 118 to mark the position of the distal end 106 of the surgical drape or the distal opening position. In some embodiments, the marking comprises a sticker, a tab near the distal end 106 of the surgical drape 102. In some embodiments, the marking is a color marking or has a distinctive shape, for example an arrow or any geometrical shape for marking the distal end 106 or the distal opening 110. In some embodiments, the marking is positioned around the distal opening.

According to some exemplary embodiments, for example as shown in FIG. 1B, the opening or aperture of the distal opening, for example distal opening 122 of surgical drape 120 is smaller than the opening or aperture of the proximal opening, for example proximal opening 112. In some embodiments, the distal opening, for example distal opening 122 is at least 50% smaller than the proximal opening 112, for example at least 50% smaller, at least 60% smaller, at least 70% smaller or any intermediate or larger percentage value.

According to some exemplary embodiments, the distal opening 122 of the surgical drape is positioned near the upper part of the surgical drape.

Exemplary Covering Process

According to some exemplary embodiments, a user, for example a technician or a physician covers surgical devices by placing a surgical drape around parts which are irrelevant to the operating procedure, while leaving relevant parts of the devices uncovered.

Figure 2:
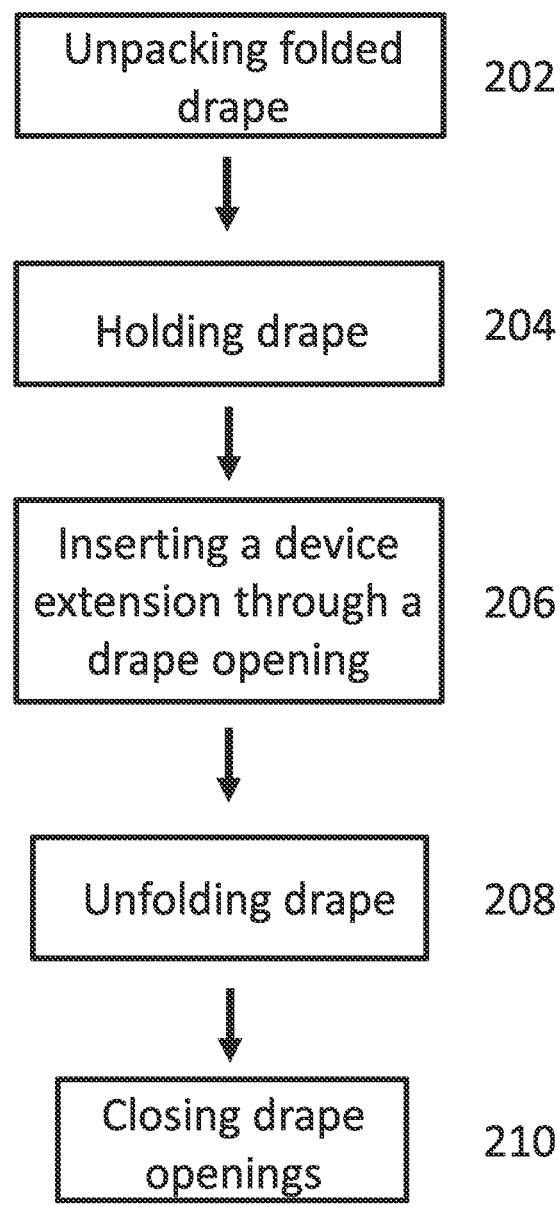
FIG. 2 is a flow chart of a process for using a surgical drape, according to some embodiments of the invention.

Reference is now made to FIG. 2, describing a process of covering a surgical device using an axially collected surgical drape, according to some exemplary embodiments of the invention.

According to some exemplary embodiments, a surgical drape is unpacked at 202. In some embodiments, the package includes an indication for the opening direction, for example not to harm the packed surgical drape. Alternatively or additionally, the package includes at least one visualized indication or marking, for the orientation of the surgical drape inside the package.

According to some exemplary embodiments, a user unpacks the surgical drape and holds the surgical drape at 204. In some embodiments, the user holds the surgical drape by at least one handling portion of an axially collapsed tubular sheath of the surgical drape. In some embodiments, the user inserts his hands or at least part of his hand into at least one axial valley fold within the surgical drape. In some embodiments, the valley fold position is marked by a visible marking, for example a color marking. Alternatively or additionally, a distal opening which is at a distal end of the surgical drape is marked by at least one visible marking, optionally a color marking.

According to some exemplary embodiments, the user holds at least one handling portion, for example a handle attached to the tubular sheath of the surgical drape, which is optionally an axially collapsed tubular sheath. In some embodiments, the handling portion is a detachable handling portion designed to detach from the foldable sheath, for example an axially collectable sheath when the sheath is axially extended.

According to some exemplary embodiments, a surgical device extension is inserted through an opening in the axially collapsed tubular sheath of the surgical drape at 206. In some embodiments, the device extension is inserted through the surgical drape when the surgical drape is at least partially axially collected. In some embodiments, the device extension is inserted until the surgical drape distal opening contacts the surgical device body. In some embodiments, the device extension is inserted first through the distal opening of the surgical drape. Alternatively, the device extension is inserted first through a proximal opening which is wider than the distal opening, and then through the distal opening. Optionally, the distal opening is closed by a distal fastener, when the distal opening contacts the surgical device body.

According to some exemplary embodiments, the opening of the tubular sheath is aligned with the extension of the surgical device prior to the insertion at 206, for example using the user's hands that are inserted into at least one fold surrounding the opening at 204.

According to some exemplary embodiments, the extension is inserted through both the proximal and distal openings of the tubular sheath.

According to some exemplary embodiments, the surgical drape is unfolded, optionally axially extended at 208. In some embodiments, the surgical drape is axially extended while covering the surgical device. In some embodiments, the surgical drape is axially extended until a desired portion of the device body is covered. Optionally, the surgical drape is axially extended until the entire device body is completely covered by the surgical drape. In some embodiments, the surgical drape is at least 70% axially extended, for example at least 70%, at least 80%, at least 90% or any intermediate or larger percentage value. In some embodiments, the surgical drape is inverted during the axially extending process.

According to some exemplary embodiments, the surgical drape covers at least part of stabilizing elements connected to the surgical device, for example a stabilizing arm, while the surgical drape axially extends at 208.

According to some exemplary embodiments, at least one opening in the surgical drape is closed at 210. In some embodiments, the distal opening is closed by at least one distal fastener positioned near or around the distal opening. Additionally, at least one additional opening of the surgical drape, for example a proximal opening is closed by a proximal fastener positioned near or around the proximal opening. Alternatively, the proximal fastener fastens a portion of the surgical drape, for example around the surgical device, optionally without closing the proximal opening of the surgical drape. In some embodiments, the distal fastener fastens the distal opening of the surgical drape around the extension of the surgical device. In some embodiments, closing the distal opening allows for example, to minimize contamination of the surgical device portions covered by the surgical drape by biological material, or biological fluids, for example blood, during a surgical procedure.

Exemplary Covering a Surgical Device

According to some exemplary embodiments, a surgical drape is packed in an axially collected state, for example to save storage space. In some embodiments, axially collecting the surgical drape reduces the volume of an axially extended surgical drape by at least 50%, for example by at least 50%, by at least 60%, by at least 70% or any intermediate or larger percentage. In some embodiments, the axially collected surgical drape contains at least one marking to indicate the orientation of the surgical drape. Alternatively or additionally, the at least one marking indicated the position of one or more openings in the surgical drape and/or the position of areas shaped or designed to be touched by a user. Optionally, the at least one marking indicates an upper and/or a lower part of the surgical drape.

Reference is now made to FIG. 3A, depicting the covering of a surgical device, according to some exemplary embodiments of the invention.

Figure 3D:
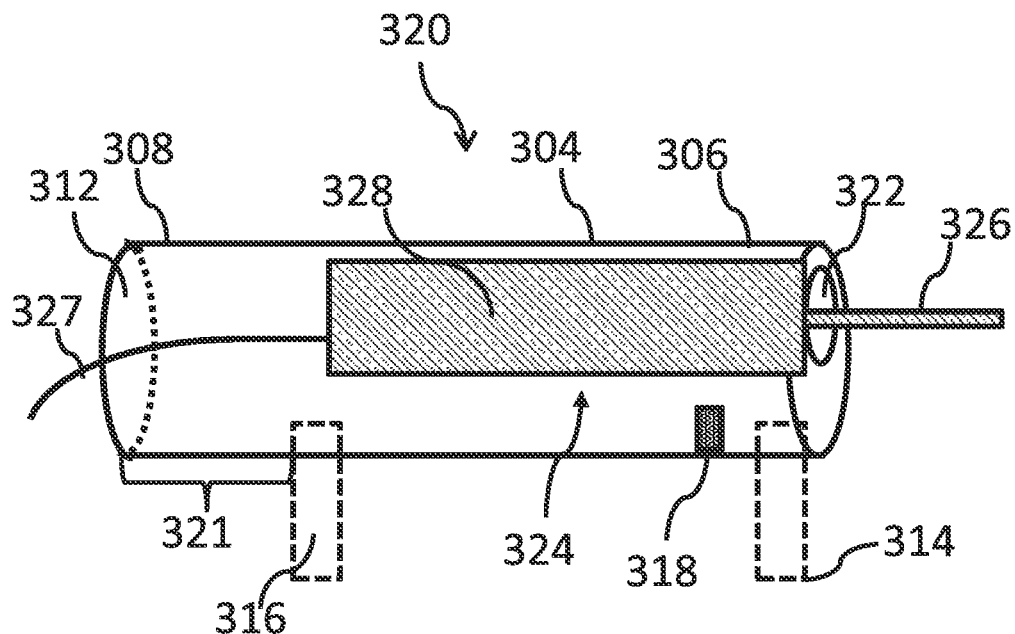
FIG. 3D is a schematic representation of an axially extended surgical drape placed at least partly around a surgical device, according to some embodiments of the invention.

According to some exemplary embodiments, a surgical drape, for example surgical drape 320 comprises a surgical drape body 304, optionally a cylindrical or tubular body, a distal end 306 and a proximal end 308. In some embodiments, the surgical body 340 comprises a tubular sheath. In some embodiments, the surgical drape body 304 comprises a distal opening 322 and a proximal opening 312. Optionally, the aperture of the distal opening is narrower than the aperture of the proximal opening 312. In some embodiments, the surgical drape 320 comprises at least one proximal fastener 316 near the proximal opening 312, for example to allow closure or narrowing of the proximal opening 312 aperture. In some embodiments, the proximal fastener 316 is spaced apart from the proximal opening 312. For example, in some embodiments, the proximal fastener 316 is positioned at an axial distance 321 of at least 10 cm from the proximal opening, for example at least 10 cm, at least 15 cm, at least 20 cm, at least 25 cm or any intermediate or larger distance, for example as shown in FIG. 3D. In some embodiments, the proximal fastener fastens a portion of the surgical drape around a body of a surgical device. In some embodiments, the length of the proximal fastener 116 is at least 10 cm, for example at least 15 cm, at least 20 cm, at least 25 cm or any intermediate or larger value.

Additionally or optionally, the surgical drape 320 comprises at least one distal fastener 314 near the distal opening 322, for example to allow closure or narrowing of the distal opening 322 aperture. In some embodiments, the distal fastener 314 is positioned in a distance of up to 15 cm from said distal opening 322, for example 15, 10, 5 cm or any intermediate or smaller value. In some embodiments, the distal fastener length is at least 15 cm, for example at least 15 cm, at least 20 cm, at least 25 cm or any intermediate or larger value.

According to some exemplary embodiments, when the surgical drape 320 is axially collected, for example as shown in FIG. 3A, the distal opening 322 is axially inverted or axially collected into an inner lumen of the surgical drape body 304. Alternatively or additionally, at least one axial valley fold, for example valley folds 315, are formed at the proximal end 308 of the surgical drape 320. In some embodiments, valley folds 315 are shaped and sized to allow insertion of at least part of a user's hand. In some embodiments, at least one marking, for example marking 318 marks the position of the distal end 306 of the surgical drape 320 and/or the position of the axially collected distal opening 322. Optionally, at least one additional marking marks the position of valley folds 315.

According to some exemplary embodiments, an extension of a surgical device 324, for example extension 326 is inserted through the distal opening 322. Optionally, a user moves the surgical drape 320 in direction 130 towards the extension 326, for example to allow insertion of the extension 326 through the distal opening 320. In some embodiments, the extension 326 is inserted into the distal opening 320 until the opening contacts a body of the surgical device, for example body 328 which is wider than the aperture of the distal opening 320.

According to some exemplary embodiments, the surgical drape 320 is moved in direction 130 to cover a desired portion of the surgical device 324. In some embodiments, the surgical drape 320 is axially extended while covering the surgical device 324.

Reference is now made to FIG. 3B, depicting a distal opening of an axially collected surgical drape in a distal view from direction 134, according to some exemplary embodiments of the invention. According to some exemplary embodiments, the surgical drape body, for example drape body 304 comprises a tubular sheath. In some embodiments, the distal opening 322 has an aperture which is smaller in at least 100% from the width of the tubular sheath, for example at least 100%, at least 200%, at least 300% or any intermediate or larger value.

Reference is now made to FIG. 3C, depicting a proximal opening and an axial valley fold of an axially collected surgical drape in a view from direction 132, according to some exemplary embodiments of the invention. In some embodiments, valley fold 317 is formed by axially collecting the proximal end of the drape body 304, at least partly into a lumen 301 of the drape body 304. In some embodiments, the valley fold 317 surrounds the lumen 301 of the drape body. In some embodiments, the width of the valley fold is sufficient to allow insertion of at least part of a user's hand, for example the fingers of a user into the valley fold.

Reference is now made to FIG. 3D, depicting an axially extended surgical drape, according to some exemplary embodiments of the invention. According to some exemplary embodiments, the surgical drape moves in direction 130 to cover a desired portion of the device 324, or optionally until the entire device body 328 is covered. In some embodiments, the surgical drape is axially extended while covering the device. Additionally or optionally, the surgical drape is axially extended until at least a portion of electrical wiring 327 of said device is covered.

Figure 3E:
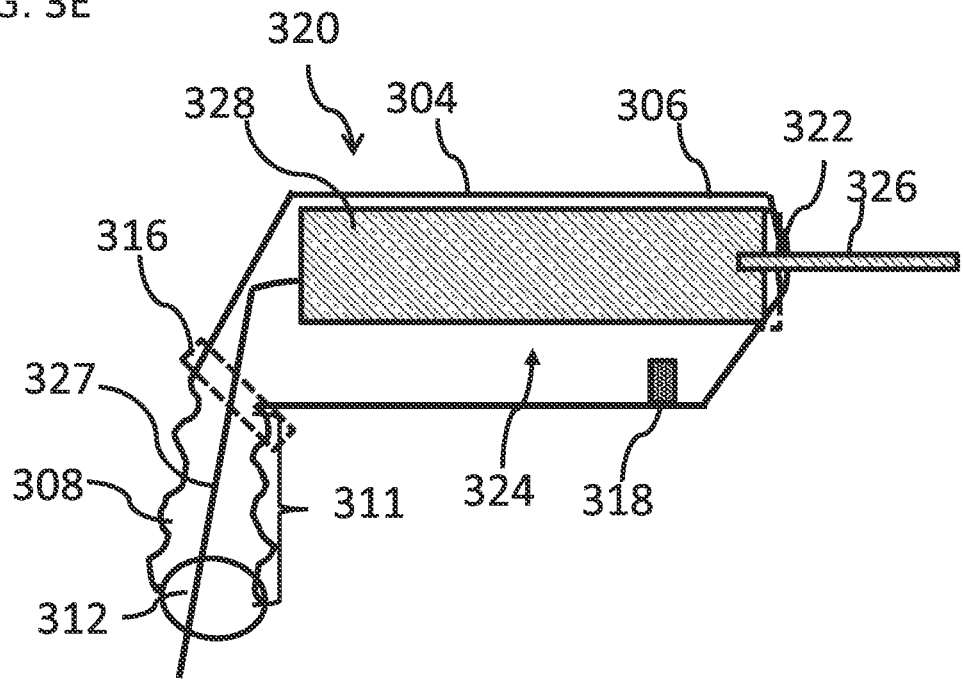
FIG. 3E is a schematic representation of an axially extended surgical drape, fastened at least partly around a surgical device, according to some embodiments of the invention.

Reference is now made to FIG. 3E, depicting a surgical drape with a closed distal opening, according to some exemplary embodiments of the invention. According to some exemplary embodiments, when the surgical drape 320 covers a desired portion of the device 324, the at least one proximal fastener 316 is fastened around a portion of the surgical drape, for example to fasten the surgical drape 320 around device 324. Additionally or optionally, the distal fastener 314 is fastened, for example to close the distal opening 322 and/or to fasten the distal opening to the device extension 326.

According to some exemplary embodiments, for example as shown in FIG. 3E, a proximal portion 311 of the surgical drape between the fastened proximal fastener 316 and the proximal opening 312 remains unfastened, and optionally partly axially collected.

According to some exemplary embodiments, when the distal fastener is fastened, and the surgical drape is axially extended a desired portion of the device body is isolated from biological fluids, for example blood. In some embodiments, when the surgical drape covers the surgical device body the device extension protrudes through the distal opening and elements connected to the device body, for example electrical wiring, cables, and/or tubes protrude through the proximal opening.

Exemplary Surgical Drape Structure

Figure 4:
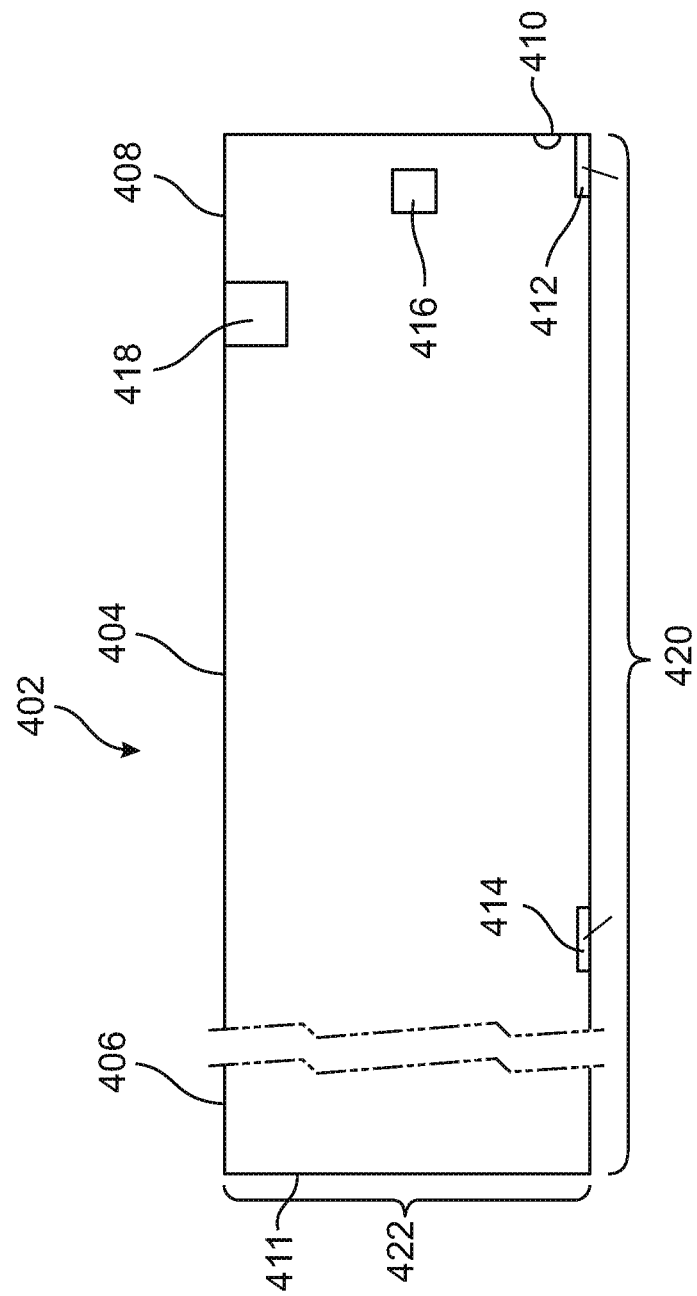
FIG. 4 is a side view schematic representation of an axially extended surgical drape, according to some embodiments of the invention.

Reference is now made to FIG. 4, which is a side view of an axially extended surgical drape, according to some exemplary embodiments of the invention.

According to some exemplary embodiments, a surgical drape, for example surgical drape 402 comprises a foldable sheath body 404, for example an axially collectable sheath body, having a proximal end 406 and a distal end 408. In some embodiments, the foldable body is a tubular body with a circular, elliptical or a rectangular cross-section. In some embodiments, the tubular body comprises a distal opening 410 and a proximal opening 411.

According to some exemplary embodiments, the axial length 420 of the surgical drape 402 is at least 20 cm, for example at least 20 cm, at least 30 cm, at least 50 cm, at least 80 cm, at least 100 cm or any intermediate or larger value. In some embodiments, largest dimension of the proximal opening 411 and/or the width 422 of surgical drape 402 is at least 15 cm, for example at least 15 cm, at least 20 cm, at least 30 cm, at least 40 cm, at least 50 cm or any intermediate or larger value. In some embodiments, the largest dimension of the distal opening 410 is at least 5 cm, for example at least 5 cm, at least 10 cm, at least 15 cm, at least 20 cm or any intermediate or larger value.

According to some exemplary embodiments, the surgical drape 402 comprises at least one visible distal marking, for example a patch or a sticker 416 attached or embedded in the drape body 404, optionally near the distal end 408. In some embodiments, the at least one visible distal marking marks the distal end of the surgical drape 402 or indicates the position of the distal end. In some embodiments, the surgical drape 402 comprises at least one visible upper marking, for example a patch or a sticker 418, attached or embedded in the upper part of the drape body 402. In some embodiments, the at least one upper marking marks the upper part of the surgical drape 402 or indicates the position of the upper part.

According to some exemplary embodiments, the surgical drape 402 comprises at least one fastener, for example distal fastener 412 near the distal opening 410. In some embodiments, the distal fastener 412 is positioned in a distance of up to 15 cm from said distal opening 410, for example 15, 10, 5 cm or any intermediate or smaller value. In some embodiments, the distal fastener length is at least 15 cm, for example 15, 20, 25 cm or any intermediate or larger value. Additionally or alternatively, the surgical drape comprises at least one fastener, for example proximal fastener 414 positioned at an axial distance of at least 15 cm from the proximal opening 411, for example at least 15 cm, at least 20 cm, at least 25 cm, at least 30 cm, at least 35 cm or any intermediate or larger value. In some embodiments, proximal fastener 414 fastens a portion of the surgical drape 402 around the surgical device, while optionally leaving a portion of the surgical drape 402 unfastened and/or at least partly axially collected, for example portion 311 in FIG. 3E. In some embodiments, the length of the proximal fastener 116 is at least 15 cm, for example at least 15 cm, at least 20 cm, at least 25 cm or any intermediate or larger value.

According to some exemplary embodiments, fastener 414 and/or fastener 412 comprises a strap optionally a Velcro strap, an adhesive tape, a clip or any fastening means that is capable of applying a force on the foldable sheath body without tearing the sheath body or any other component of the surgical drape 402.

Exemplary Axially Collected Surgical Drape with Valley Folds

Figure 5A:
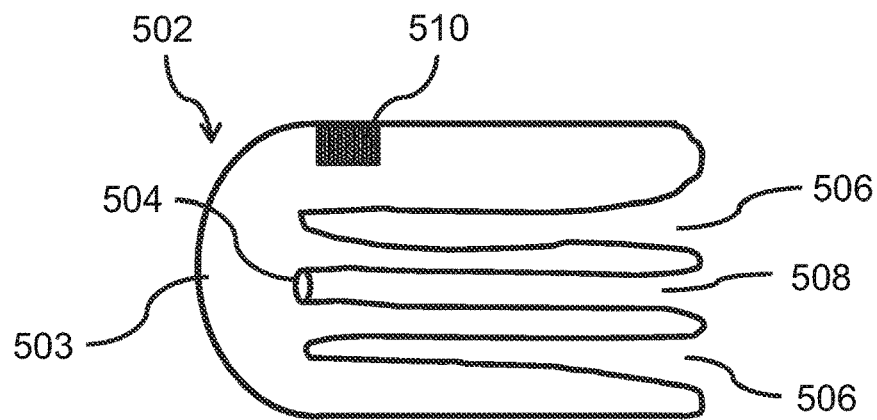
FIG. 5A is a schematic representation of an axially collected surgical drape, according to some embodiments of the invention.

Reference is now made to FIG. 5A depicting a schematic representation of an axially collected surgical drape, according to some exemplary embodiments of the invention.

According to some exemplary embodiments, surgical drape 502 comprises a proximal opening 503 and a distal opening 504, which has a narrower aperture compared to the aperture of the proximal opening 503. In some embodiments, when surgical drape 502 is axially collected the distal opening 504 is axially collected into a lumen of the surgical drape 502. In some embodiments, the distal opening 504 is axially collected, optionally by forming an axial valley fold 508, until it is positioned near the proximal opening 503, for example as shown in FIG. 5A. In some embodiments, at least one additional axial valley fold 506 is formed. In some embodiments, valley fold 506 is shaped to allow the insertion of at least part of a user's hand, for example the fingers. In some embodiments, the valley fold 506 surrounds the distal opening 504, and allows, for example the insertion of hands on both sides of the distal opening 504. A possible advantage of placing the hands of a user on both sides of the distal opening, is that it allows better and/or easier alignment of the surgical device extension with the distal opening.

In some embodiments, when the surgical drape 502 is axially collected, the distal opening 504 is positioned in a distance of less than 10 cm from the proximal opening 503, for example 10, 8, 5 cm or any intermediate or smaller value.

According to some exemplary embodiments, the surgical drape comprises at least one marking 510 located, for example on the upper part of the surgical drape or the tubular sheath of the surgical drape. In some embodiments, the marking 510 indicates the position of the upper part of the surgical drape and/or the position of the distal opening.

Figure 5B:
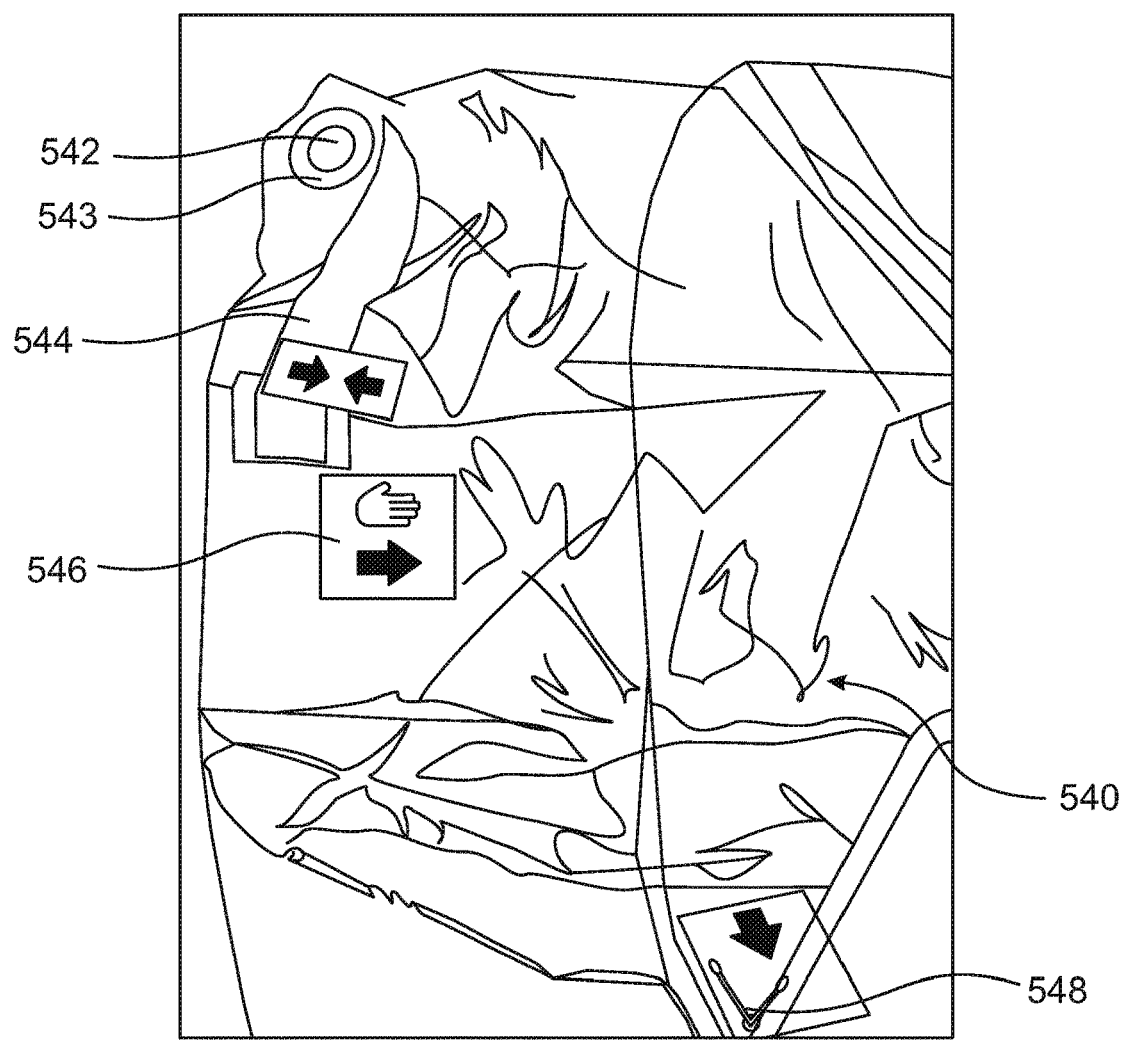
FIG. 5B is a schematic drawing of an axially collected surgical drape, according to some embodiments of the invention.

Reference is now made to FIG. 5B depicting a partially axially collected surgical drape having at least one valley fold, according to some exemplary embodiments of the invention.

According to some exemplary embodiments, an axially collected surgical drape, for example surgical drape 540, comprises at least one opening 542 which is sized and shaped to allow insertion of a surgical device extension through the opening 542 into the surgical drape 540. In some embodiments, the opening 542 is positioned at the distal end of the surgical drape, facing the surgical device. In some embodiments, the at least one opening 542 is positioned near the upper part of the surgical drape. In some embodiments, the opening is marked by a colored opening marking 543, which is optionally designed to be visible through the axially collected surgical drape. Optionally, the colored opening marking surrounds the opening 542.

According to some exemplary embodiments, the axially collected surgical drape 540 comprises at least one marking, for example marking 546, for example for indicating the position of the folds fitted for the insertion of at least part of the user's hand. Additionally or alternatively, the axially collected surgical drape comprises at least one marking for indication the proximal opening of the axially collected surgical drape 540, for example marking 548.

According to some exemplary embodiments, the axially collected surgical drape 540 comprises at least one distal fastener, for example distal fastener 544 positioned adjacent to the distal opening, for example opening 542. In some embodiments, the distal fastener comprises a strap with an adhesive portion. In some embodiments, the distal fastener 544 is positioned in a distance of up to 15 cm from said distal opening 542, for example up to 15 cm, up to 10 cm, up to 5 cm or any intermediate or smaller value. In some embodiments, the distal fastener length is at least 15 cm, for example at least 15 cm, at least 20 cm, at least 25 cm or any intermediate or larger value. Optionally, the distal fastener is colored with a distinctive color, for example to allow easily visualization of the distal fastener during the covering process. Additionally, the axially collected surgical drape 540 comprises at least one proximal fastener, for closing the proximal opening of the surgical drape.

Exemplary Process of a Surgical Device with a Robotic Arm

Figure 6:
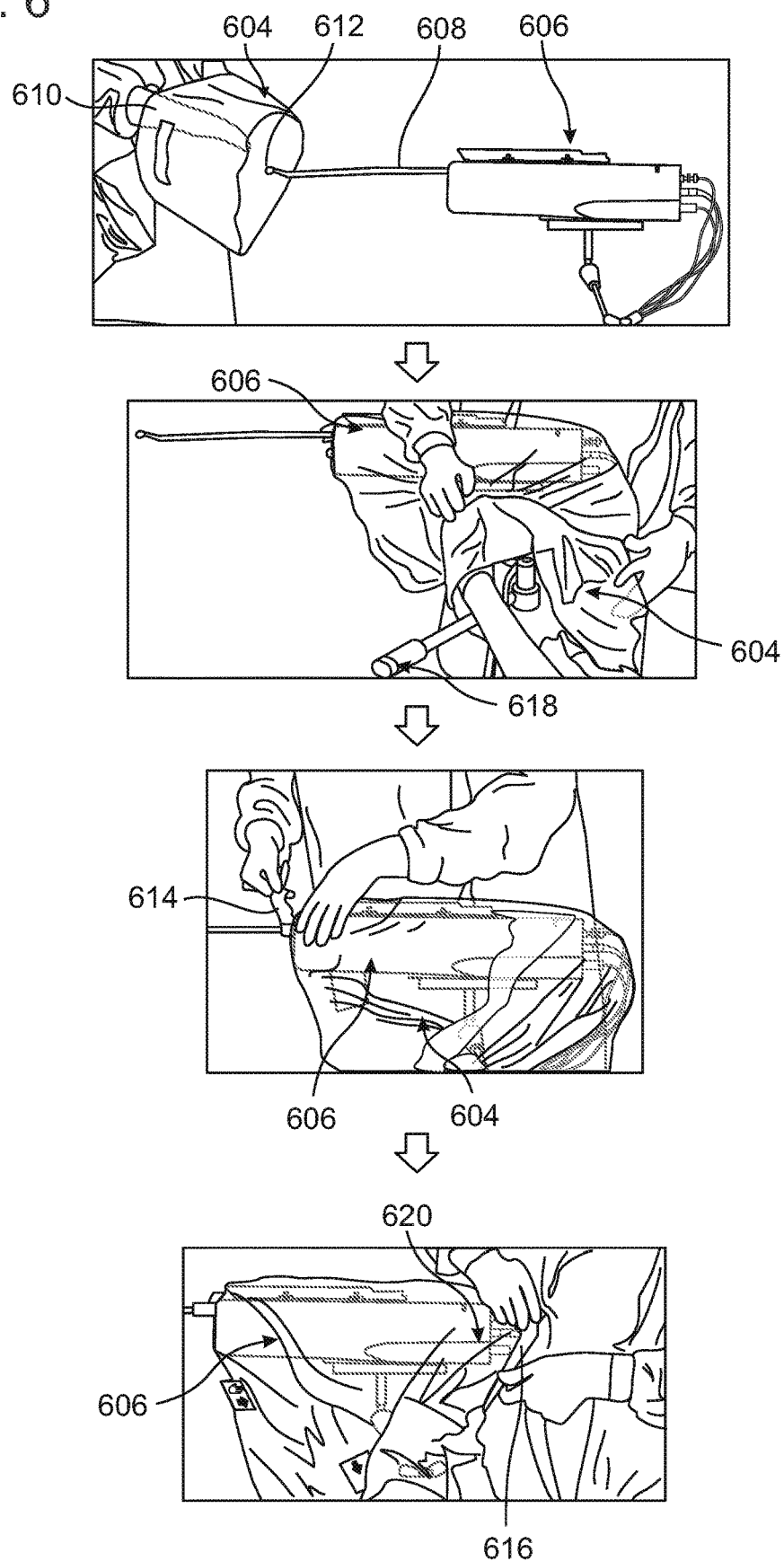
FIG. 6 are drawings showing a process for covering a surgical device by axially extending a surgical drape, according to some embodiments of the invention.

Reference is now made to FIG. 6 depicting a process for covering a surgical device having a robotic arm while axially extending a surgical drape, according to some exemplary embodiments of the invention.

According to some exemplary embodiments, for example as shown in the first drawing of FIG. 6, a user inserts at least part of his hand 610 into a valley fold in an axially collected surgical drape 604. In some embodiments, the user inserts a robotic arm 608 of surgical device 606 through a distal opening 612 of the surgical drape 604. In some embodiments, the user inserts the robotic arm 608 into the distal opening 612 while facing the surgical device, for example to allow an easier orientation between the surgical arm and the distal opening.

According to some exemplary embodiments, for example as shown in the second drawing of FIG. 6, the surgical drape 604 is axially extended during the coverage of the surgical device 606. In some embodiments, the surgical drape is a tubular surgical drape which axially extends during the coverage of the surgical device 606 and at least part of a fixation arm 618 connected to the surgical device 606. In some embodiments, the fixation arm 618 connects the surgical device 606 to a bed of a patient. Alternatively, the fixation arm 618 connects the surgical device 606 to the ceiling or a wall.

According to some exemplary embodiments, for example as shown in the third and fourth drawings of FIGS. 6, when the desired portion of the surgical device is covered, a distal fastener 614 attached to the surgical drape 604 is fastened to close the distal opening. Optionally, the distal fastener fastens the surgical drape 604 or the distal opening of the surgical drape to the robotic arm. Additionally, a proximal fastener 616 attached to the surgical drape 604 is fastened around the surgical device 606, for example around the surgical device base 620.

Exemplary Surgical Drape with Concertina Folds

Figure 7A:
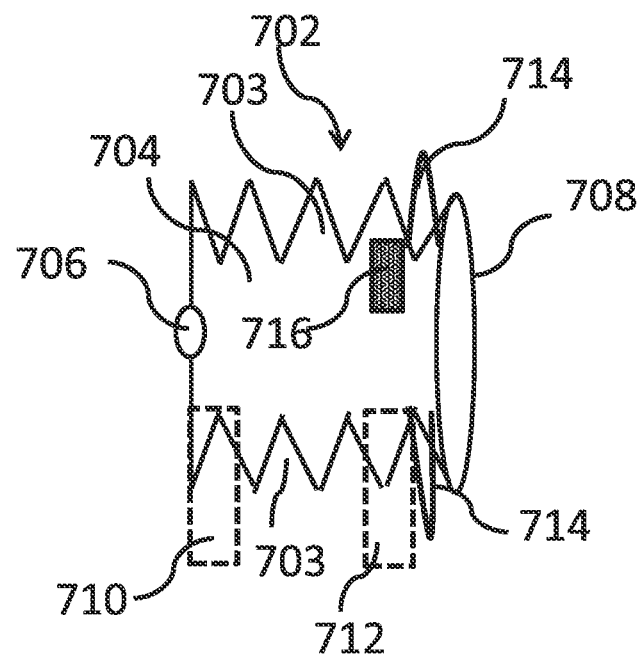
FIGS. 7A-7C are schematic representations of surgical drape with a plurality of concertina folds, according to some embodiments of the invention.
Figure 7B:
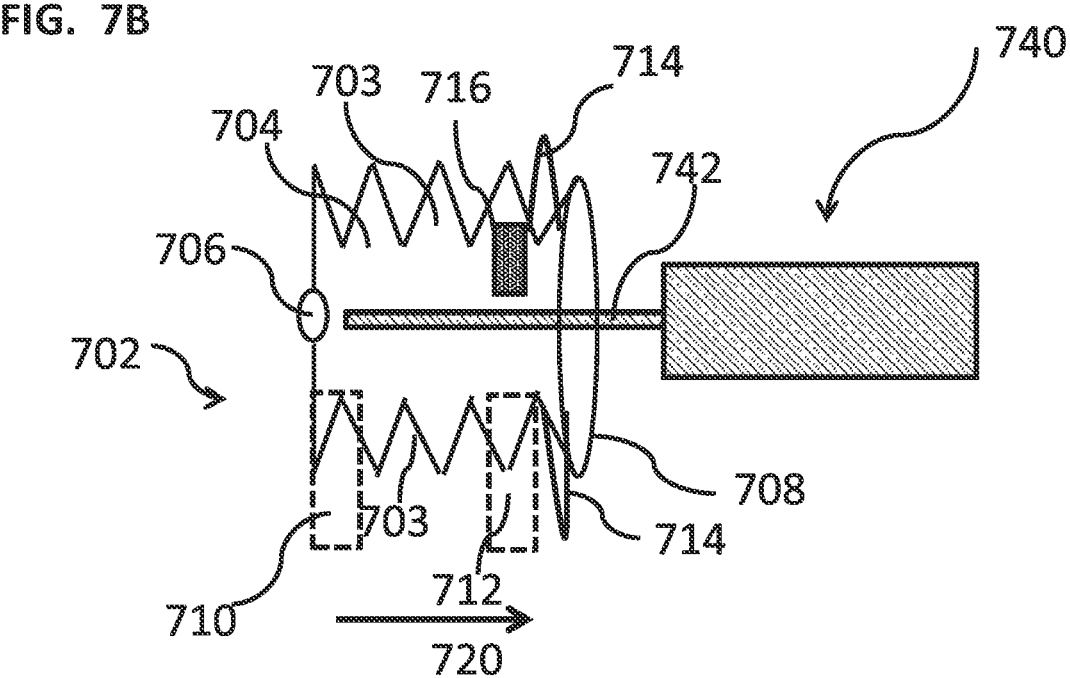
Figure 7C:
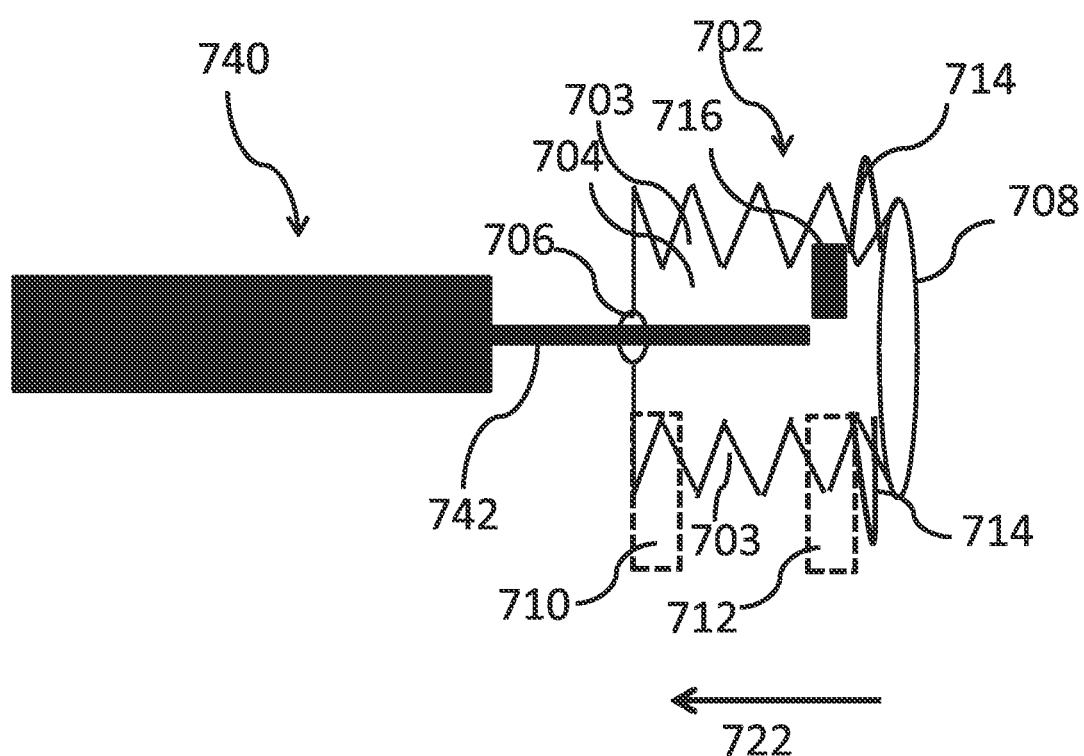

Reference is now made to FIGS. 7A-7C depicting a surgical drape with concertina folds, according to some exemplary embodiments of the invention.

According to some exemplary embodiments, a surgical drape 702 comprises an axially collectable cover, for example foldable cover 704, which is optionally a tubular sheath having a distal opening 706 and a proximal opening 708. In some embodiments, the proximal opening 708 has a wider aperture than the aperture of the distal opening 706. In some embodiments, the foldable cover comprises a plurality of concertina folds 703, also termed zig-zag folds. Optionally, the concertina folds 703 are radial folds.

According to some exemplary embodiments, the surgical drape comprises at least one handling portion, for example handling portions 714. In some embodiments, the handling portions 714 comprising a handle or a strap sized and shaped to be gripped by the hands of a user. In some embodiments, the handling portions 714 are attached to the outer surface of the foldable cover 704. Optionally, the gripping members 714 are detachable handling portions. In some embodiments, the handling portions detach from the foldable cover, for example once the desired portion of the surgical device is covered.

According to some exemplary embodiments, the surgical drape 702 comprises at least one distal fastener 710 for closing the distal opening 706, and at least one proximal fastener 712 for closing the proximal opening 708. In some embodiments, the distal fastener 710 is positioned in a distance of up to 15 cm from said distal opening 706, for example 15, 10, 5 cm or any intermediate or smaller value. In some embodiments, the distal fastener and/or the proximal fastener length is at least 15 cm, for example at least 15 cm, at least 20 cm, at least 25 cm or any intermediate or larger value. In some embodiments, the surgical drape comprises at least one marking, for example marking 716 for marking the position of the handling portions 714 and/or the position of the proximal opening 708. Alternatively or additionally, the marking marks the position of the distal opening 706. Optionally, the marking is colored, for example to allow visualization of the marking through the foldable cover 704 which is optionally at least partially transparent.

Reference is now made to FIG. 7B depicting the insertion of a surgical device through a proximal opening of an axially collected surgical drape, according to some exemplary embodiments of the invention. According to some exemplary embodiments, the surgical drape 702 comprises a plurality of radial concertina folds 703. In some embodiments, for example as shown in FIG. 7B, when the surgical drape 702 is axially collected, the extension 742 of the surgical device 740 is inserted through the proximal opening 708 and then through the distal opening 706. In some embodiments, the surgical drape axially extends while covering a desired portion of the surgical device 740. In some embodiments, for example as shown in FIG. 7B, the surgical device is forwarded in direction 720, while inserting the extension 742 through the proximal opening. In some embodiments, a user, holds the surgical drape 702 using handling portions 714, while forwarding the drape in direction 720, for example to cover the surgical device 740.

Reference is now made to FIG. 7C, depicting the insertion of a surgical device through a distal opening of an axially collected surgical drape, according to some exemplary embodiments. In some embodiments, the surgical drape 702 comprises a plurality radial concertina folds 703, when the surgical drape 702 is axially collected. In some embodiments, a user advances the axially collected surgical drape in direction 722 optionally by holding the handling portions 714. In some embodiments, the extension 742 of the surgical device 740 enters through the distal opening 706 of the surgical drape 702. In some embodiments, the surgical drape 702 is inverted while covering the surgical device 740.

As used herein with reference to quantity or value, the term "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A surgical drape for covering a surgical device having an extension, the extension comprising a robotic arm comprising a proximal portion seated in a non-extended portion of the surgical device, the surgical drape comprising:

a thin-walled flexible tube having proximal and distal tube-ends, wherein:

said proximal tube-end is open to define a proximal opening sized to allow passage therethrough of at least a lengthwise portion of the non-extended portion of the surgical device without stretching, and said distal tube-end is mostly-closed and includes a distal aperture smaller than the proximal opening, wherein said distal aperture is larger than a width of the extension of the surgical device and sized to allow insertion therethrough of the extension without requiring contact therebetween, and is sized to prevent passage therethrough of the non-extended portion of the surgical device without stretching, wherein said thin-walled flexible tube provides a straight-configuration where: (i) said thin-walled flexible tube is straight; (ii) a central axis of said thin-walled flexible tube is straight and passes through respective centers of said proximal and distal tube-ends; and (iii) said distal aperture is radially offset from said central axis of said thin-walled flexible tube, and wherein said thin-walled flexible tube is axially foldable to form at least one valley fold surrounding said distal tube-end, wherein a fold line of each said at least one valley fold is defined between two axially disposed portions of said thin-walled flexible tube, said at least one valley fold sized and shaped for insertion of hands of a user into said at least one valley fold on two sides of said distal tube-end; and at least one distal fastener positioned near said distal tube-end, and configured to close said aperture about the extension of the surgical device.

2. The surgical drape according to claim 1, wherein: (i) said thin-walled flexible tube is configured to be axially collected when folded, (ii) said distal tube-end is axially collected into a lumen defined by said thin-walled flexible tube and (iii) when axially collected, said thin-walled flexible tube forms said at least one valley fold.

3. The surgical drape of claim 2, wherein a length of said surgical drape when axially collected is at least 50% smaller than a length of said surgical drape in an axially extended state.

4. The surgical drape of claim 1, comprising at least one handling portion configured to allow manipulation of said thin-walled flexible tube by hand.

5. The surgical drape of claim 4, wherein said at least one handling portion comprises one or more of: said at least one valley fold, at least one slot formed in a surface of said thin-walled flexible tube, a strap and/or a handle connected to said thin-walled flexible tube.

6. The surgical drape of claim 1 wherein, when said surgical drape is in an axially collected configuration, said fold line is disposed at an interior location relative to another portion of said thin-walled flexible tube.

7. The surgical drape of claim 6, wherein said another portion of said thin-walled flexible tube is a surface of said thin-walled flexible tube after deployment.

8. The surgical drape of claim 1, wherein said thin-walled flexible tube radially folds to form a plurality of concertina folds.

9. The surgical drape of claim 1, comprising at least one proximal fastener positioned at an axial distance of at least 10 cm from said proximal opening.

10. The surgical drape of claim 1, wherein said thin-walled flexible tube has a circular, elliptical or a rectangular cross-section.

11. The surgical drape of claim 1, wherein said distal aperture is at least 50% smaller than said proximal opening.

12. The surgical drape of claim 1, wherein said at least one distal fastener is positioned within a distance of up to 15 cm from said distal aperture.

13. The surgical drape of claim 1, wherein said at least one valley fold comprises at least said one handling portion configured to allow manipulation of said thin-walled flexible tube by the hands of the user.

14. The surgical drape of claim 1, including at least one proximal fastener positioned near said proximal tube-end, and configured to close said opening of said proximal tube-end.

15. The surgical drape of claim 1,
wherein said surgical drape includes a visible marking on said thin-walled flexible tube near said distal tube-end, said visible marking located:
on a circumferential portion of said thin-walled flexible tube adjacent said distal aperture,
on a circumferential portion of said thin-walled flexible tube opposite said distal aperture, or
surrounding said distal aperture.

16. The surgical drape of claim 1, wherein said at least one valley fold is axially oriented relative to said drape, and wherein said at least one valley fold is oriented, sized and shaped for insertion of hands of a user in an axial direction into said at least one valley fold on two sides of said distal aperture.

17. The surgical drape of claim 1, wherein said at least one valley fold is oriented, sized, and shaped for insertion of hands of a user into said at least one valley fold on two sides of said distal aperture, said orientation of said at least one valley fold being such that it has an opening directed toward said distal.

18. The surgical drape of claim 1, wherein said at least one valley fold is oriented, sized, and shaped for insertion of hands of a user in an axial direction into said at least one valley fold on two sides of said distal aperture, said orientation of said at least one valley fold being such that it has an opening directed toward said distal aperture.

19. The surgical drape of claim 1, wherein said thin walled flexible tube includes an outer surface and an inner surface, wherein each said valley fold is disposed between portions of said outer surface of said thin walled flexible tube.

20. A method for covering a surgical device having an extension, the extension comprising a robotic arm including a proximal portion seated in a non-extended portion of the surgical device, the method comprising:
providing a surgical drape according to claim 1 in a state in which said thin-walled flexible tube is axially collected;
inserting the extension of said surgical device through said distal aperture and into a lumen of said thin-walled flexible tube;
axially extending said thin-walled flexible tube while to covering at least a portion of the non-extended portion of said surgical device; and
closing said distal aperture about the extension by said at least one distal fastener.

21. The method of claim 20, comprising:
aligning said distal aperture with said extension of said surgical device introducing at least part of a hand of a user into said at least one valley fold in said thin walled flexible tube when in the axially collected state prior to said inserting.

22. The method of claim 20, wherein said closing comprises fastening a portion of said thin-walled flexible tube by at least one proximal fastener.

23. The method of claim 20, wherein said inserting comprises, inserting said extension through said distal aperture into said lumen of said thin-walled flexible tube and out of said lumen through said proximal opening of said thin-walled flexible tube.

24. The method of claim 20, wherein said thin walled flexible tube includes an outer surface and an inner surface, said inserting including inserting the extension of the surgical device into the lumen such that said outer surface of said thin walled flexible tube contacts the surgical device.

25. Surgical apparatus comprising:
a. a surgical device having an extension, the extension comprising a robotic arm comprising a proximal portion seated in a non-extended portion of the surgical device, the non-extended portion having a transverse cross-section at least 5 times larger than a transverse cross-section of the extension; and
b. a surgical drape according to claim 12, the distal aperture sized to allow insertion therethrough of the extension without requiring contact therebetween and to prevent passage therethrough of a non-extended portion of the surgical device without stretching, the proximal opening sized to allow passage therethrough of at least a length wise portion of the surgical device with stretching.

26. A method for deploying the surgical apparatus of claim 25, the method comprising:
providing the surgical drape in a state in which said thin-walled flexible tube is axially collected;
inserting the extension of said surgical device through said distal aperture and into a lumen of said thin-walled flexible tube; and
axially extending said thin-walled flexible tube to cover at least a portion of the non-extended portion of said surgical device.

27. The method of claim 25, additionally comprising: closing said distal aperture about the extension by said at least one distal fastener.

28. Surgical apparatus comprising:
   a. a surgical device comprising a robotic arm extending distally from a body portion of the surgical device, the body portion having a transverse cross-section at least 5 times larger than a transverse cross-section of the robotic arm; and
   b. a surgical drape comprising a thin-walled flexible tube having proximal and distal tube-ends, wherein:
      i. the proximal tube-end is open to define a proximal opening sized to permit passage therethrough of at least a lengthwise portion of the body portion without requiring contact therebetween,
      ii. the distal tube-end is mostly closed and includes a distal aperture smaller than the proximal opening and larger than the transverse cross-section of the robotic arm, the distal aperture being sized to allow insertion therethrough of the robotic arm without requiring contact therebetween, and to prevent passage therethrough of the body portion without stretching, and
      iii. the thin-walled flexible tube is arrangeable or extendable to assume a straight configuration in which a straight central axis of the thin-walled flexible tube passes through respective centers of the proximal and distal tube-ends, and the distal aperture is radially offset from the central axis of the thin-walled flexible tube.

29. A method for deploying the surgical apparatus of claim 28, the method comprising:
   i. providing the surgical drape in a state in which the thin-walled flexible tube is axially collected by folding;
   ii. inserting the robotic arm through the distal aperture and into a lumen of the thin-walled flexible tube; and
   iii. axially extending the thin-walled flexible tube to cover at least a portion of the body portion of the surgical device.

* * * * *